US008287971B2

(12) United States Patent
Beakler

(10) Patent No.: US 8,287,971 B2
(45) Date of Patent: Oct. 16, 2012

(54) SPALTED WOOD VENEERS, SPALTED ENGINEERED WOOD FLOORING AND METHOD OF MAKING

(75) Inventor: Brian W. Beakler, York, PA (US)

(73) Assignee: Armstrong World Industries, Inc., Lancaster, PA (US)

( * ) Notice: Subject to any disclaimer, the term of this patent is extended or adjusted under 35 U.S.C. 154(b) by 811 days.

(21) Appl. No.: 11/901,361

(22) Filed: Sep. 17, 2007

(65) Prior Publication Data

US 2008/0226847 A1 Sep. 18, 2008

(51) Int. Cl.
*A21G 1/00* (2006.01)
*C12P 1/02* (2006.01)

(52) U.S. Cl. .......................................... 428/22; 435/171

(58) Field of Classification Search .................... 428/22; 435/171
See application file for complete search history.

(56) References Cited

OTHER PUBLICATIONS

Croan "Evaluation of White-Rot Fungal Growth on Southern Yellow Pine Wood Chips Pretreated with Blue-Stain Fungi" The International Research Group on Wood Preservation Section 1 Biology 31st Annual Meeting Kona, Hawaii, USA pp. 1-9 May 2000.*

Andrew Hilton; Spatting, A Fungus Amongus; http://hiltonhandcraft.com/Articles/Spalting_a_Fungus_Amongus.asp; pp. 1-11, Pub Date for this web site article Mar. 12, 2007.

White-rot Fungus; http://www.hawaii.edu/abrp/Technologies/fungus.html; pp. 1-3, Pub Date for this web site article Jul. 7, 2007.

The Spalted Wood—One Man's Junk Another Man's Prize; http://www.dnr.state.oh.us/forestry/Industries/spaltedwood.htm; pp. 1-3, Pub Date for this web site article Mar. 8, 2007.

Tips for creating spalted maple; http://www.woodweb.com/knowledge_base/Tips_for_creating_spalted_maple.html?printfriendly; Jan. 4, 2001; pp. 1-2.

Intentional Spalting; http://www.woodweb.com/knowledge_base/Intentional_Spalting.html; Jun. 23, 2005; pp. 1-5.

Alan Lacer; Spalted Wood; http://www.alanlacer.com/articles/spalting.html; pp. 1-5, Pub Date this web site article Mar. 8, 2007.

Producing Spalted Wood; USDA Forest Service; Mar. 2004; pp. 1-2; MO-1; Madison, WI.

Blue Stain; USDA Forest Service; May 2002; II-2; Madison, WI.

* cited by examiner

*Primary Examiner* — Herbert J Lilling
(74) *Attorney, Agent, or Firm* — McNeeds Wallace & Nurick LLC

(57) ABSTRACT

Spalted wood veneer, which can be used in the commercial production of engineered wood flooring having a spalted wood veneer decorative layer, is produced by forming a wood veneer piece, inoculating the wood veneer piece with spalting spores, subjecting the inoculated veneer piece to a predetermined environment, then inspecting the inoculated veneer piece to determine the degree of spalting, and when a desired degree of spalting is reached, deterring continued spalting.

21 Claims, No Drawings

SPALTED WOOD VENEERS, SPALTED ENGINEERED WOOD FLOORING AND METHOD OF MAKING

The present invention is related to spalted wood veneers, spalted engineered wood flooring and the method of making the veneers and flooring.

BACKGROUND OF THE INVENTION

Spalted wood occurs naturally in forests in felled logs and trees which have been infected with spalt fungus (a combination of white rot and blue stain). The spalting makes the wood brittle and difficult to cut into lumber. Therefore, it has not been possible to cut the spalted wood into veneers.

According to the American National Standards Institute, a veneer is a thin sheet of wood, rotary cut, sliced, or sawed from a log, bolt or flitch. A veneer is referred to as a ply when assembled. The formation of spalted veneers would permit the manufacture of spalted engineered wood flooring having a spalted wood veneer decorative layer.

Naturally occurring spalted maple is traditionally used by artisans in lathe produced turnings, e.g. bowls and vases. While spalted solid wood floors have been made from lumber pieces cut from spalted logs, it has not been possible to cut the spalted logs into veneers for use in making engineered wood and engineered wood floors. If the decay progresses too far, the wood becomes punky, soft and spongy, stringy, ring-shaked, pitted or crumbly.

Spalting is a decay process in certain wood species that gives the wood a unique blotchy appearance having dark lines. White rot is a decay mechanism that yields thin distinctive lines with broad lighter colored areas in between the lines. White rot is caused by, white rot decay fungi. The white rot attacks the cellulose and lignin giving the wood a whitish appearance and multicolored streaks of black, pink and gray. The white rot spores are typically airborne.

Blue stain does not contribute to the decay of the wood but does yield a yellow, orange, red, blue, black or brown coloration. It is caused by microscopic fungi that infect only the sapwood. The blue stain fungi are normally spread by spores that are carried into the wood by insects.

SUMMARY OF THE INVENTION

It is an object of the invention is to provide a spalted wood veneer, particularly a veneer that can be produced in a time frame to enable commercial production.

Another object of the invention is to provide engineered wood flooring, i.e., a multi-layered wood flooring product, having a spalted wood veneer decorative layer.

It is also an object of the invention to provide a method to manufacture a spalted wood veneer.

It is a further object of the present invention to provide a method to manufacture a spalted engineered wood flooring having a spalted wood veneer decorative layer.

DETAILED DESCRIPTION OF THE INVENTION

To form the spalted veneer, green (wet) wood is cut into veneers and then inoculated with the white rot (e.g. *Phanerochaete chyrsosporium*) and/or blue stain (e.g. *Ceratocystis tenella*) spores by coating the surfaces of the veneer with a solution containing the spores. Both of the major surfaces of the veneers can be efficiently coated with a roll coat system. Other means of inoculating the cut veneers is to spray the major surfaces of the veneers with a solution containing the white rot and/or blue stain spores. The environment of the impregnated veneers can be controlled to promote the rapid growth of the spalting and then stopped when the desired degree of spalting is achieved.

The invention is directed to any species of wood which can be cut into veneers and spalted. The wood species that can be used include maple, elm, beech, birch, buckeye, basswood, sycamore, apple, and the hickories. Red oak and white oak will also spalt. While walnut will spalt, it is dark in color and more difficult to observe.

White rot grows best at temperatures of from about 70° F. to about 90° F. and a wood moisture content of about 30% in an oxygen rich atmosphere. The best conditions for blue stain are temperatures between about 60° F. and about 150° F. and a wood moisture content of about 20% to about 30% in an oxygen rich atmosphere. For efficient growth of the white rot and blue stain spores, the wood veneer should have a moisture content of about 20% to about 40% during the spalting process Therefore, the inoculated veneers can be stacked into a chamber in which a preferred environment for spalting the veneer of about 50° F. to about 100° F. with about 50% R1-1 to about 90% RH is maintained. No growth of the white rot is seen below about 50° F. A more preferred environment for processing the spalted veneers is a temperature of from about 70° F. to about 90° F. and about 70% RH to about 90% RH in an oxygen rich atmosphere.

Prior to loading the inoculated veneers into the chamber, the chamber could be sterilized with an ultraviolet light treatment to kill any other spores. The spalting process may take days, weeks or months, depending upon the type and condition of the wood and the environmental conditions. Samples are removed frequently and inspected to determine when the spalting process should be stopped. It is desired to allow the spalting to proceed to a point where the appearance is pleasing, but the structure of the veneer has not been overly weakened.

The spalting process can be halted by drying the veneers at a temperature of at least 130° F. After the spalting process has been stopped, the spalted veneers can be stabilized and/or stiffened by filling the spalted areas with waxes, oils, glues or impregnation chemicals, such as acrylics. The veneers are then glued to the engineered platform or base, and then tongue and groove edges, including locking tongue and groove edges, are typically machined into the engineered wood piece.

The invention claimed is:

1. A method of commercial production of a spalted wood veneer comprising:

forming a wood veneer, then inoculating the wood veneer with spalting spores, then periodically inspecting the inoculated wood veneer to determine the degree of spalting, and then when a desired degree of spalting is reached, deterring continued spalting.

2. The method of claim 1, wherein the wood veneer is inoculated with spores selected from the group consisting of white rot spores, blue stain spores and a combination of white rot spores and blue stain spores.

3. The method of claim 2, wherein the wood veneer is inoculated with a solution containing spores selected from the group consisting of white rot spores, blue stain spores and a combination of white rot spores and blue stain spores.

4. The method of claim 3, wherein the wood veneer is inoculated by applying the solution containing the spores with a roll coater.

5. The method of claim 1, wherein a plurality of inoculated wood veneers are stacked in a chamber.

6. The method of claim 5, wherein the chamber is sterilized prior to stacking the wood veneers in the chamber.

7. The method of claim 6, wherein the chamber is sterilized by subjecting the chamber to ultraviolet light.

8. The method of claim 1, wherein the inoculated wood veneer is subjected to a predetermined environment having an average temperature of from about 50° F. to about 100° F. and a relative humidity of from about 50% RH to about 90% RH.

9. The method of claim 8, wherein the predetermined environment is oxygen rich.

10. The method of claim 8, wherein the predetermined environment has an average temperature of from about 70° F. and about 90° F. and a relative humidity of from about 70% RH to about 50% RH.

11. The method of claim 10, wherein the predetermined environment is oxygen rich.

12. The method of claim 1, wherein the wood veneer has a moisture content of about 20% to about 40% during the spalting.

13. The method of claim 1, wherein continued spalting is deterred by raising the temperature of the wood veneer to at least 130° F.

14. The method of claim 1, wherein the spalted wood veneer is coated with a wax, an oil, a glue or an impregnation chemical.

15. The method of claim 14, wherein the impregnation chemical is an acrylic.

16. The method of claim 3, wherein the wood veneer is inoculated by spraying major surfaces of the wood veneer with the solution containing the spores.

17. The method of claim 3, wherein the wood veneer is inoculated by coating surfaces of the wood veneer with the solution containing the spores.

18. The method of claim 1, further comprising gluing the wood veneer to a base after deterring continued spalting to form a spalted engineered wood flooring.

19. The method of claim 1, wherein the wood veneer is a species of wood selected from the group consisting of maple, elm, beech, birch, buckeye, basswood, sycamore, apple, hickory, red oak, white oak, and walnut.

20. The method of claim 1, wherein the wood veneer is formed from a log, bolt, or flitch.

21. The method of claim 18, wherein the base is machined to form tongue and groove edges.

* * * * *